(12) United States Patent
Meijles

(10) Patent No.: US 8,374,818 B2
(45) Date of Patent: Feb. 12, 2013

(54) SYSTEM, METHOD AND APPARATUS FOR CALIBRATING INSPECTION TOOLS

(75) Inventor: Peter Meijles, San Jose, CA (US)

(73) Assignee: Affymetrix, Inc., Santa Clara, CA (US)

( * ) Notice: Subject to any disclaimer, the term of this patent is extended or adjusted under 35 U.S.C. 154(b) by 412 days.

(21) Appl. No.: 12/643,864

(22) Filed: Dec. 21, 2009

(65) Prior Publication Data

US 2010/0161266 A1    Jun. 24, 2010

Related U.S. Application Data

(60) Provisional application No. 61/139,121, filed on Dec. 19, 2008.

(51) Int. Cl.
*G01C 17/38* (2006.01)

(52) U.S. Cl. .................. 702/94; 702/97; 702/158

(58) Field of Classification Search .............. 702/94, 702/97, 158; 430/31; 355/53, 55; 257/48; 118/712
See application file for complete search history.

(56) References Cited

U.S. PATENT DOCUMENTS

| | | | |
|---|---|---|---|
| 4,087,672 A | 5/1978 | Yi | |
| 4,545,018 A | 10/1985 | Clements et al. | |
| 4,735,877 A | 4/1988 | Kato et al. | |
| 4,825,034 A | 4/1989 | Auvert | |
| 4,861,144 A | 8/1989 | Russell | |
| 4,866,243 A | 9/1989 | Sakane et al. | |
| 4,868,126 A | 9/1989 | Schwartz | |
| 4,886,968 A | 12/1989 | Ohnishi et al. | |
| 4,918,611 A | 4/1990 | Shyu et al. | |
| 4,980,114 A | 12/1990 | Satake et al. | |
| 4,981,783 A | 1/1991 | Augenlicht | |
| 5,040,047 A | 8/1991 | Cole et al. | |
| 5,091,652 A | 2/1992 | Mathies et al. | |
| 5,157,506 A * | 10/1992 | Hannah | 382/167 |
| 5,211,805 A | 5/1993 | Srinivasan | |
| 5,216,247 A | 6/1993 | Wang et al. | |
| 5,224,240 A | 7/1993 | Smith | |
| 5,262,128 A | 11/1993 | Leighton et al. | |
| 5,274,240 A | 12/1993 | Mathies et al. | |
| 5,293,363 A | 3/1994 | Takeshita | |
| 5,315,375 A | 5/1994 | Allen | |
| 5,381,224 A | 1/1995 | Dixon et al. | |
| 5,424,186 A | 6/1995 | Fodor et al. | |
| 5,424,841 A | 6/1995 | Van Gelder et al. | |
| 5,459,325 A | 10/1995 | Hueton et al. | |

(Continued)

FOREIGN PATENT DOCUMENTS

| | | |
|---|---|---|
| EP | 0050159 | 8/1986 |
| EP | 0557719 | 8/1995 |

(Continued)

OTHER PUBLICATIONS

Alexay et al., "Fluorescence scanner employing a macro scanning objective," Fluorescence Detection IV, SPIE, 2705: 63-72 (1996).

(Continued)

*Primary Examiner* — Michael Nghiem
*Assistant Examiner* — Elias Desta
(74) *Attorney, Agent, or Firm* — Affymetrix, Inc.

(57) ABSTRACT

The present invention relates to systems and methods for examining a number of components that have been assembled onto a substrate. In general, the invention relates to the calibration of inspection tools for inspecting components on the substrate. In particular, the invention relates to the calibration of inspection tools for detecting the accuracy of the array pegs positions on an assembled HTA plate.

18 Claims, 7 Drawing Sheets

U.S. PATENT DOCUMENTS

| | | |
|---|---|---|
| 5,464,960 A | 11/1995 | Hall et al. |
| 5,578,832 A | 11/1996 | Trulson et al. |
| 5,585,639 A | 12/1996 | Dorsel et al. |
| 5,610,754 A | 3/1997 | Gheen et al. |
| 5,631,734 A | 5/1997 | Stern et al. |
| 5,646,411 A | 7/1997 | Kain et al. |
| 5,672,880 A | 9/1997 | Kain |
| 5,719,391 A | 2/1998 | Kain |
| 5,721,435 A | 2/1998 | Troll |
| 5,737,121 A | 4/1998 | Dixon |
| 5,760,951 A | 6/1998 | Dixon et al. |
| 5,772,656 A | 6/1998 | Klopotek et al. |
| 5,800,992 A | 9/1998 | Fodor et al. |
| 5,810,930 A | 9/1998 | Eom et al. |
| 5,880,465 A | 3/1999 | Boettner et al. |
| 5,895,915 A | 4/1999 | DeWeerd et al. |
| 5,910,390 A | 6/1999 | Hatanaka et al. |
| 5,922,612 A | 7/1999 | Alder et al. |
| 5,981,956 A | 11/1999 | Stern |
| 6,066,448 A | 5/2000 | Wohlstadter et al. |
| 6,069,984 A | 5/2000 | Sadler et al. |
| 6,075,613 A | 6/2000 | Schermer et al. |
| 6,090,545 A | 7/2000 | Wohlstadter et al. |
| 6,140,044 A | 10/2000 | Besemer et al. |
| 6,143,152 A | 11/2000 | Simpson et al. |
| 6,157,402 A | 12/2000 | Torgeson |
| 6,185,030 B1 | 2/2001 | Overbeck |
| 6,191,802 B1 | 2/2001 | Kessler |
| 6,201,639 B1 | 3/2001 | Overbeck |
| 6,207,960 B1 | 3/2001 | Stern |
| 6,218,803 B1 | 4/2001 | Montagu |
| 6,225,625 B1 | 5/2001 | Pirrung et al. |
| 6,259,524 B1 | 7/2001 | Hofstraat et al. |
| 6,355,934 B1 | 3/2002 | Osgood et al. |
| 6,381,013 B1 | 4/2002 | Richardson |
| 6,383,412 B1 | 5/2002 | Hasegawa |
| 6,472,671 B1 | 10/2002 | Montagu |
| 6,514,768 B1 | 2/2003 | Guire et al. |
| 6,531,864 B2 | 3/2003 | Montagu |
| 6,583,424 B2 | 6/2003 | Staton et al. |
| 6,596,186 B2 | 7/2003 | Yasuda et al. |
| 6,631,147 B2 | 10/2003 | Taniguchi et al. |
| 6,687,395 B1 | 2/2004 | Dietz et al. |
| 6,740,871 B1 | 5/2004 | Staton et al. |
| 6,788,414 B1 | 9/2004 | Yeung et al. |
| 6,794,424 B2 | 9/2004 | Holcomb et al. |
| 6,813,567 B2 | 11/2004 | Weiner et al. |
| 6,984,828 B2 | 1/2006 | Montagu |
| 7,033,754 B2 | 4/2006 | Chee et al. |
| 7,045,756 B2 | 5/2006 | Kinney et al. |
| 7,067,819 B2 | 6/2006 | Janik |
| 7,135,143 B2 | 11/2006 | Abbott et al. |
| 7,173,256 B2 | 2/2007 | Fox |
| 7,222,025 B2 | 5/2007 | Weiner et al. |
| 7,317,415 B2 | 1/2008 | Kaiser |
| 7,324,677 B2 | 1/2008 | Minor |
| 7,406,391 B2 | 7/2008 | Miles |
| 7,502,096 B2 * | 3/2009 | Tempelaars et al. ............ 355/53 |
| 7,689,022 B2 | 3/2010 | Weiner et al. |
| 2002/0133080 A1 | 9/2002 | Apruzzese et al. |
| 2005/0206893 A1 | 9/2005 | Montagu |
| 2007/0012885 A1 | 1/2007 | Montagu |
| 2007/0190566 A1 | 8/2007 | Montagu |
| 2009/0296058 A1 * | 12/2009 | Slotboom et al. ............... 355/53 |

FOREIGN PATENT DOCUMENTS

| | | |
|---|---|---|
| EP | 1254392 | 1/2008 |
| JP | 09203865 | 8/1997 |
| JP | 10153529 | 6/1998 |
| WO | WO 98/49537 | 11/1998 |
| WO | WO 99/00689 | 7/1999 |
| WO | WO 99/36760 | 7/1999 |
| WO | WO 99/47964 | 9/1999 |

OTHER PUBLICATIONS

Epstein et al., "High-density, microsphere-based fiber optic DNA microarrays," Biosensors and Bioelectronics, 18: 541-546 (2003).

* cited by examiner

SYSTEM, METHOD AND APPARATUS FOR CALIBRATING INSPECTION TOOLS

FIELD OF THE INVENTION

The invention relates to sensors and sensor packages. More particularly, the invention relates to the manufacturing and packaging of biological microarrays. In accordance with one aspect of the invention, systems and methods for inspecting components that have been assembled onto a substrate are provided for the fabrication of high density polymer arrays and assortments of high density arrays. In particular, the invention relates to the calibration of inspection tools for inspecting the location of components on a substrate. More specifically, one aspect of the invention relates to the calibration of an inspection tool for detecting the accuracy of the positions of the assembled array pegs on an HTA plate.

BACKGROUND OF THE INVENTION

Genetic information is critical in continuation of life processes. Life is substantially information based and genetic content controls the growth and reproduction of organisms. The amino acid sequences of polypeptides, which are critical features of all living systems, are encoded by the genetic material of the cell. Further, the properties of these polypeptides, e.g., as enzymes, functional proteins, and structural proteins, are determined by the sequence of amino acids which make them up. As structure and function are integrally related, many biological functions may be explained by elucidating the underlying structural features which provide those functions, and these structures are determined by the underlying genetic information in the form of polynucleotide sequences. In addition to encoding polypeptides, polynucleotide sequences can also be specifically involved in, for example, the control and regulation of gene expression.

The study of this genetic information has proved to be of great value in providing a better understanding of life processes, as well as diagnosing and treating a large number of disorders. In particular, disorders which are caused by mutations, deletions or repeats in specific portions of the genome, may be readily diagnosed and/or treated using genetic techniques. Similarly, disorders caused by external agents may be diagnosed by detecting the presence of genetic material which is unique to the external agent, e.g., bacterial or viral DNA.

High-throughput devices have been developed for processing a large number of microarrays and providing more flexibility. Substantial progress has been made in the fabrication and placement of microarrays. For example, millions of different sequences may be fabricated on a single substrate of about 1.28 $cm^2$ in only a small fraction of the time required by conventional methods. Such improvements make these substrates practical for use in various applications, such as biomedical research, clinical diagnostics, and other industrial markets, as well as the emerging field of genomics, which focuses on determining the relationship between genetic sequences and human physiology.

As commercialization of such substrates becomes widespread, additional methods for microarray quality control and inspections are desired.

BRIEF SUMMARY OF THE INVENTION

An embodiment of the invention provides systems, method, and devices related to calibration methods of inspection tools. In one aspect of the invention, the calibration of inspection tools for inspecting the location of components on a substrate is provided. Merely by way of example, the invention is described as it applies to the calibration of an inspection tool for detecting the positions of pegs with biological probe arrays on a plate, but it should be recognized that the invention has a broader range of applicability. The calibration method includes supporting a calibration substrate. The calibration substrate comprises a plurality of component fiducials that indicate the theoretical location of the component on the substrate to be inspected. The method involves using a robot to place the camera over the first component fiducial by moving the camera in the X,Y direction. The first component fiducial on the calibration substrate is imaged using a vision system. The X,Y positions of the component fiducial are then measured. The calibration offset values for the X,Y positions are calculated by utilizing the measured X,Y values. The moving, imaging, measuring and calculating steps are repeated for each component fiducial until the pairs of offset values for all the component fiducials are calculated. The calibration offset values are then placed and stored into an XY map. These calibration offset values are used during the inspection of the components of the plate. According to a preferred embodiment, the calibration substrate is made of glass and the plurality of component fiducials are etched onto the glass substrate. According to another preferred embodiment, the plurality of component fiducials on the calibration substrate are within 3 microns of their theoretical location.

BRIEF DESCRIPTION OF THE DRAWINGS

The accompanying non-limiting drawings, which are incorporated in and form a part of this specification, illustrate embodiments of the invention and, together with the description, serve to explain the principles of the invention.

FIG. 1A depicts an example of a sensor peg. FIG. 1B depicts a sensor peg with an o-ring.

FIG. 2A shows a support member with tapered sides wherein the sensor can be attached to a larger surface area. FIG. 2B depicts a support member with a block post and block platform in which the sensor can be attached to either end. FIG. 2C depicts a support member with a cylindrical post and a square platform in which the sensor can be attached.

Figure 1A:
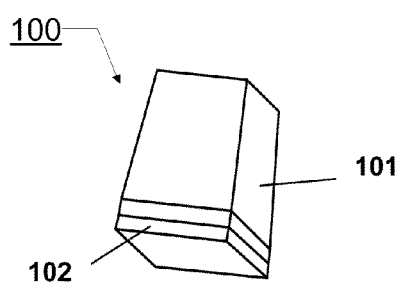
FIGS. 1A and 1B illustrate examples of a sensor peg.

The figures are merely examples, which should not unduly limit the scope of the claims. One of ordinary skill in the art would recognize many variations, alternatives, and modifications.

DETAILED DESCRIPTION OF THE INVENTION

I. General Description

Reference will now be made in detail to exemplary embodiments of the invention. While the invention will be described in conjunction with the exemplary embodiments, they are not intended to limit the invention to these embodiments. On the contrary, the invention encompasses alternatives, modifications and equivalents that are within the spirit and scope of the invention.

The invention relates to diverse fields impacted by the nature of molecular interaction, including chemistry, biology, medicine and diagnostics. Methods disclosed herein are advantageous in various fields such as those in which genetic information is required quickly such as in clinical diagnostic laboratories or in large-scale undertakings such as the Human Genome Project.

The invention has many embodiments and relies on many patents, applications and other references for details known to those of the art. Therefore, when a patent, application, or other reference is cited or repeated below, it should be understood that the entire disclosure of the document cited is incorporated by reference in its entirety for all purposes as well as for the proposition that is recited. All documents, e.g., publications and patent applications, cited in this disclosure, including the foregoing, are incorporated herein by reference in their entireties for all purposes to the same extent as if each of the individual documents were specifically and individually indicated to be so incorporated herein by reference in its entirety.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including, but not limited to, mammals, plants, bacteria, or cells derived from any of the above.

Throughout this disclosure, various aspects of this invention can be presented in a range format. It should be understood that when a description is provided in range format, this is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This applies regardless of the breadth of the range.

The practice of the invention may employ, unless otherwise indicated, conventional techniques and descriptions of organic chemistry, polymer technology, molecular biology (including recombinant techniques), cell biology, biochemistry, and immunology, which are within the skill of one of skill in the art. Such conventional techniques include polymer array synthesis, hybridization, ligation, and detection of hybridization using a detectable label. Specific illustrations of suitable techniques are provided by reference to the examples hereinbelow. However, other equivalent conventional procedures may also be employed. Such conventional techniques and descriptions may be found in standard laboratory manuals, such as *Genome Analysis: A Laboratory Manual Series (Vols. I-IV)*, *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995), *Biochemistry*, 4th Ed., Freeman, New York, Gait, *Oligonucleotide Synthesis: A Practical Approach*, (1984), IRL Press, London, Nelson and Cox (2000), Lehninger, Principles of Biochemistry, $3^{rd}$ Ed., W.H. Freeman Pub., New York, N.Y., and Berg et al. (2002), *Biochemistry*, $5^{th}$ Ed., W.H. Freeman Pub., New York, N.Y., all of which are herein incorporated in their entirety by reference for all purposes.

The invention may employ solid substrates, including arrays in some embodiments. Methods and techniques applicable to polymer (including protein) array synthesis have been described in U.S. Ser. No. 09/536,841 (abandoned), WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, and in PCT Applications Nos. PCT/US99/00730 (International Publication No. WO 99/36760) and PCT/US01/04285 (International Publication No. WO 01/58593), which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the invention include, but are not limited to, those that are commercially available from Affymetrix (Santa Clara, Calif.) under the brand name GENECHIP®. Example arrays are shown on the website at affymetrix.com.

The invention contemplates many uses for polymers attached to solid substrates. These uses include, but are not limited to, gene expression monitoring, profiling, library screening, genotyping and diagnostics. Methods of gene expression monitoring and profiling are described in U.S. Pat. Nos. 5,800,992, 6,013,449, 6,020,135, 6,033,860, 6,040,138, 6,177,248 and 6,309,822. Genotyping methods, and uses thereof, are disclosed in U.S. patent application Ser. No. 10/442,021 (abandoned) and U.S. Pat. Nos. 5,856,092, 6,300, 063, 5,858,659, 6,284,460, 6,361,947, 6,368,799, 6,333,179, and 6,872,529. Other uses are described in U.S. Pat. Nos. 5,871,928, 5,902,723, 6,045,996, 5,541,061, and 6,197,506.

The invention also contemplates sample preparation methods in certain embodiments. Prior to, or concurrent with, genotyping, the genomic sample may be amplified by a variety of mechanisms, some of which may employ PCR. (See, for example, *PCR Technology: Principles and Applications for DNA Amplification*, Ed. H. A. Erlich, Freeman Press, NY, N.Y., 1992; *PCR Protocols: A Guide to Methods and Applications*, Eds. Innis, et al., Academic Press, San Diego, Calif., 1990; Mattila et al., *Nucleic Acids Res.*, 19:4967, 1991; Eckert et al., *PCR Methods and Applications*, 1:17, 1991; PCR, Eds. McPherson et al., IRL Press, Oxford, 1991; and U.S. Pat. Nos. 4,683,202, 4,683,195, 4,800,159 4,965,188, and 5,333, 675, each of which is incorporated herein by reference in their entireties for all purposes. The sample may also be amplified on the array. (See, for example, U.S. Pat. No. 6,300,070 and U.S. patent application Ser. No. 09/513,300 (abandoned), all of which are incorporated herein by reference).

Other suitable amplification methods include the ligase chain reaction (LCR) (see, for example, Wu and Wallace, *Genomics*, 4:560 (1989), Landegren et al., *Science*, 241:1077 (1988) and Barringer et al., *Gene*, 89:117 (1990)), transcription amplification (Kwoh et al., *Proc. Natl. Acad. Sci. USA*, 86:1173 (1989) and WO 88/10315), self-sustained sequence replication (Guatelli et al., *Proc. Nat. Acad. Sci. USA*, 87:1874 (1990) and WO 90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909 and 5,861,245) and nucleic acid based sequence amplification (NABSA). (See also, U.S. Pat. Nos. 5,409,818, 5,554,517, and 6,063,603, each of which is incorporated herein by reference). Other amplification methods that may be used are described in, for instance, U.S. Pat. Nos. 6,582,938, 5,242,794, 5,494,810, and 4,988,617, each of which is incorporated herein by reference.

Additional methods of sample preparation and techniques for reducing the complexity of a nucleic sample are described in Dong et al., *Genome Research*, 11:1418 (2001), U.S. Pat. Nos. 6,361,947, 6,391,592, 6,632,611, 6,872,529 and 6,958,225, and in U.S. patent application Ser. No. 09/916,135 (abandoned).

Methods for conducting polynucleotide hybridization assays have been well developed in the art. Hybridization assay procedures and conditions will vary depending on the application and are selected in accordance with known general binding methods, including those referred to in Maniatis et al., *Molecular Cloning: A Laboratory Manual*, 2$^{nd}$ Ed., Cold Spring Harbor, N.Y., (1989); Berger and Kimmel, Methods in Enzymology, Guide to Molecular Cloning Techniques, Vol. 152, Academic Press, Inc., San Diego, Calif. (1987); Young and Davism, *Proc. Nat'l. Acad. Sci.*, 80:1194 (1983). Methods and apparatus for performing repeated and controlled hybridization reactions have been described in, for example, U.S. Pat. Nos. 5,871,928, 5,874,219, 6,045,996, 6,386,749, and 6,391,623 each of which are incorporated herein by reference.

The invention also contemplates signal detection of hybridization between ligands in certain embodiments. (See, U.S. Pat. Nos. 5,143,854, 5,578,832, 5,631,734, 5,834,758, 5,936,324, 5,981,956, 6,025,601, 6,141,096, 6,185,030, 6,201,639, 6,218,803, and 6,225,625, U.S. patent application Ser. No. 10/389,194 (U.S. Patent Application Publication No. 2004/0012676, allowed on Nov. 9, 2009) and PCT Application PCT/US99/06097 (published as WO 99/47964), each of which is hereby incorporated by reference in its entirety for all purposes).

The practice of the invention may also employ conventional biology methods, software and systems. Computer software products of the invention typically include, for instance, computer readable medium having computer-executable instructions for performing the logic steps of the method of the invention. Suitable computer readable medium include, but are not limited to, a floppy disk, CD-ROM/DVD/DVD-ROM, hard-disk drive, flash memory, ROM/RAM, magnetic tapes, etc. The computer executable instructions may be written in a suitable computer language or combination of several computer languages. Basic computational biology methods which may be employed in the invention are described in, for example, Setubal and Meidanis et al., *Introduction to Computational Biology Methods*, PWS Publishing Company, Boston, (1997); Salzberg, Searles, Kasif, (Ed.), *Computational Methods in Molecular Biology*, Elsevier, Amsterdam, (1998); Rashidi and Buehler, *Bioinformatics Basics: Application in Biological Science and Medicine*, CRC Press, London, (2000); and Ouelette and Bzevanis *Bioinformatics: A Practical Guide for Analysis of Gene and Proteins*, Wiley & Sons, Inc., 2$^{nd}$ ed., (2001). (See also, U.S. Pat. No. 6,420,108).

The invention may also make use of various computer program products and software for a variety of purposes, such as probe design, management of data, analysis, and instrument operation. (See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170).

Computer software products are provided to control various active components, temperature and measurement devices. The system can be conveniently controlled by any programmable device, preferably a digital computer such as a Dell personal computer. The computers typically have one or more central processing unit coupled with a memory. A display device such as a monitor is attached for displaying data and programming. A printer may also be attached. A computer readable medium such as a hard drive or a CD ROM can be attached. Program instructions for controlling the liquid handling can be stored on these devices.

Additionally, the invention encompasses embodiments that may include methods for providing genetic information over networks such as the internet, as disclosed in, for instance, U.S. patent application Ser. Nos. 10/197,621 (U.S. Patent Application Publication No. 20030097222), 10/063,559 (U.S. Patent Application Publication No. 20020183936, abandoned), 10/065,856 (U.S. Patent Application Publication No. 20030100995, abandoned), 10/065,868 (U.S. Patent Application Publication No. 20030120432, abandoned), 10/328,818 (U.S. Patent Application Publication No. 20040002818, abandoned), 10/328,872 (U.S. Patent Application Publication No. 20040126840, abandoned), 10/423,403 (U.S. Patent Application Publication No. 20040049354, abandoned), and 60/482,389 (expired).

II. Definitions

The term "array" as used herein refers to an intentionally created collection of molecules which can be prepared either synthetically or biosynthetically. The molecules in the array can be identical or different from each other. The array can assume a variety of formats, for example, libraries of soluble molecules; libraries of compounds tethered to resin beads, silica chips, or other solid supports.

The term "array plate" as used herein refers to a body having a plurality of arrays in which each microarray is separated by a physical barrier resistant to the passage of liquids and forming an area or space, referred to as a well, capable of containing liquids in contact with the probe array.

The term "biopolymer" or sometimes refer by "biological polymer" as used herein is intended to mean repeating units of biological or chemical moieties. Representative biopolymers include, but are not limited to, nucleic acids, oligonucleotides, amino acids, proteins, peptides, hormones, oligosaccharides, lipids, glycolipids, lipopolysaccharides, phospholipids, synthetic analogues of the foregoing, including, but not limited to, inverted nucleotides, peptide nucleic acids, Meta-DNA, and combinations of the above.

The term "biopolymer synthesis" as used herein is intended to encompass the synthetic production, both organic and inorganic, of a biopolymer. Related to a bioploymer is a "biomonomer".

The term "combinatorial synthesis strategy" as used herein refers to an ordered strategy for parallel synthesis of diverse polymer sequences by sequential addition of reagents which may be represented by a reactant matrix and a switch matrix, the product of which is a product matrix. A reactant matrix is a l column by m row matrix of the building blocks to be added. The switch matrix is all or a subset of the binary numbers, preferably ordered, between 1 and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, and then illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other spatially selective deprotecting or activating agents to remove protecting groups from materials for addition of other materials such as amino acids.

The term "fiducial" or "fiduciary marker" is used herein as an object used in the field of view of an imaging system which appears in the image produced, for use as a point of reference or a measure.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "microtiter plates" as used herein refers to arrays of discrete wells that come in standard formats (96, 384 and 1536 wells) which are used for examination of the physical, chemical or biological characteristics of a quantity of samples in parallel.

The term "nucleic acid library" or sometimes refer by "array" as used herein refers to an intentionally created collection of nucleic acids which can be prepared either synthetically or biosynthetically and screened for biological activity in a variety of different formats (for example, libraries of soluble molecules; and libraries of oligos tethered to resin beads, silica chips, or other solid supports). Additionally, the term "array" is meant to include those libraries of nucleic acids which can be prepared by spotting nucleic acids of essentially any length (for example, from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "nucleic acids" as used herein may include any polymer or oligomer of pyrimidine and purine bases, preferably cytosine, thymine, and uracil, and adenine and guanine, respectively. See Albert L. Lehninger, PRINCIPLES OF BIOCHEMISTRY, at 793-800 (Worth Pub. 1982). Indeed, the invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

The term "oligonucleotide" or sometimes refer by "polynucleotide" as used herein refers to a nucleic acid ranging from at least 2, preferable at least 8, and more preferably at least 20 nucleotides in length or a compound that specifically hybridizes to a polynucleotide. Polynucleotides of the invention include sequences of deoxyribonucleic acid (DNA) or ribonucleic acid (RNA) which may be isolated from natural sources, recombinantly produced or artificially synthesized and mimetics thereof. A further example of a polynucleotide of the invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "probe" as used herein refers to a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (for example, opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

The term "reader" or "plate reader" as used herein refers to a_device which is used to identify hybridization events on an array, such as the hybridization between a nucleic acid probe on the array and a fluorescently labeled target. Readers are known in the art and are commercially available through Affymetrix, Santa Clara Calif. and other companies. Generally, they involve the use of an excitation energy (such as a laser) to illuminate a fluorescently labeled target nucleic acid that has hybridized to the probe. Then, the reemitted radiation (at a different wavelength than the excitation energy) is detected using devices such as a CCD, PMT, photodiode, or similar devices to register the collected emissions. See U.S. Pat. No. 6,225,625.

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

The term "solid support", "support", and "substrate" as used herein are used interchangeably and refer to a material or group of materials having a rigid, semi-rigid surface or flexible surface. In one embodiment, the surface may be a combination of materials where at least one layer is flexible. Surfaces on the solid substrate can be composed of the same material as the substrate. In another embodiment, the substrate may be fabricated form a single material or be fabricated of two or more materials. Thus, the surface may be composed of any of a wide variety of materials, for example, polymers, plastics, resins, polysaccharides, silica or silica-based materials, carbon, metals, inorganic glasses, membranes, or any of the above-listed substrate materials. In a further embodiment, the surface can be supported by a flexible material or a solid material. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates The term "surface" or "active probe surface" or "target surface" as used herein refers to the area of the microarray to be analyzed with reagents.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

The term "wafer" as used herein refers to a substrate having surface to which a plurality of arrays are bound. In a preferred embodiment, the arrays are synthesized on the surface of the substrate to create multiple arrays that are physically separate. In one preferred embodiment of a wafer, the arrays are physically separated by a distance of at least about 0.1, 0.25, 0.5, 1 or 1.5 millimeters. The arrays that are on the wafer may be identical, each one may be different, or there may be some combination thereof. Particularly preferred wafers are about 8"×8" and are made using the photolithographic process.

The term "well plate" as used herein refers to a body with a plurality of cavities open at both wherein the cavities form an area or space referred to as a well wherein each well will hold an array.

III. Specific Embodiments

Some embodiments of the invention are systems and methods for calibrating inspection tools to inspect components assembled onto a substrate. In one aspect of the invention, systems, methods, and computer software products are provided for calibrating the inspection tools to inspect microarray devices related to biological assays. Merely by way of example, the invention is described as it applies to inspecting the positions of probe arrays on plates, but it should be recognized that the invention has a broader range of applicability.

Some conventional techniques for inspecting components are often required to inspect the location of a component in the X, Y coordinates. Some products have higher position requirements due to the nature of the product, for example a probe array product. Besides locating the position of the array in the X,Y position, the theta location of the array can be critical. In one aspect of the invention, systems, methods, and computer software products are provided for a calibration method of an inspection tool to locate the positions of probe arrays on a plate.

In another aspect of the invention, methods, devices, systems and computer software products for automated array assembly are provided. For example, certain systems, methods, and computer software products are described herein using exemplary implementations of biological materials such as, for instance, Affymetrix GENECHIP® probe arrays on the GENECHIP® HT Array (HTA) Plate. In an alternative embodiment of the invention, the inspection tool can be attached to the HTA plate packaging equipment. Each peg on the HTA plates (96 peg plates) can be required to be at a theoretical location on the peg plate, within certain x, y, and theta tolerances. These peg measurements can be performed by the inspection tool. The inspection tool is calibrated, according to an embodiment of the invention, such that each array peg can be precisely measured on the plate. Various alternatives, modifications and equivalents are possible. These systems, methods, and products may be applied with respect to many other types of probe arrays and, more generally, with respect to numerous parallel biological assays produced in accordance with other conventional technologies and/or produced in accordance with techniques that may be developed in the future. For example, the systems, methods, and products described herein may be applied to parallel assays of nucleic acids, PCR products generated from cDNA clones, proteins, antibodies, or many other biological materials. These materials may be disposed on slides (as typically used for spotted arrays), on substrates employed for GENECHIP® arrays, or on beads, bead arrays, optical fibers, or other substrates or media, which may include polymeric coatings or other layers on top of slides or other substrates. Moreover, the probes need not be immobilized in or on a substrate, and, if immobilized, need not be disposed in regular patterns or arrays. For convenience, the term "probe array" will generally be used broadly hereafter to refer to all of these types of arrays and parallel biological assays. Certain embodiments of the invention are described in the simplified figures of this application.

Sensor Packages Having Sensor Pegs

In one aspect of the invention, methods and apparatus for packaging sensors are provided. These methods and apparatus are particularly useful for packaging microarrays. The following describes the exemplary design, materials, manufacturing processes and application protocols used for processing a sensor peg as an illustration of the various aspect of the invention. The sensor pegs, sensor strips and sensor plates have been described in U.S. Patent Application Publication 20060088863, which is incorporated herein by reference in its entirety for all purposes.

Sensor Peg

Figure 1B:
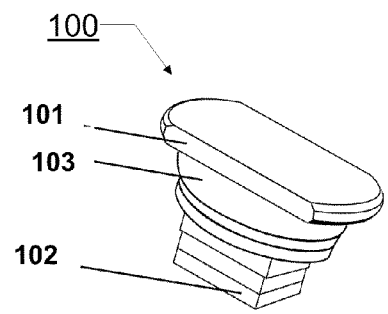
Figure 2A:
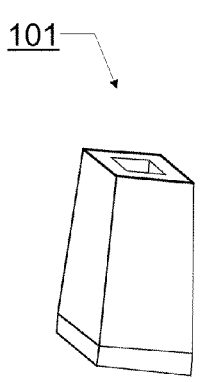
FIGS. 2A to 2C illustrate various shapes of a support member.
Figure 2B:
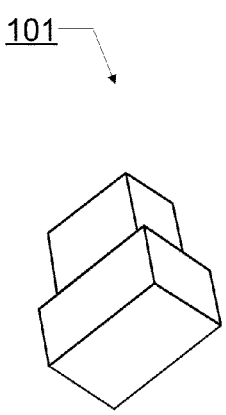
Figure 2C:
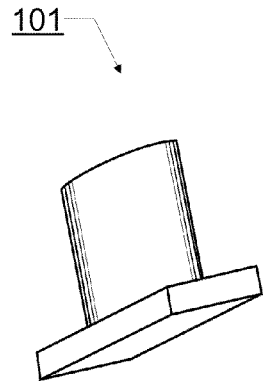

According to one aspect of the invention, a sensor peg (100) as depicted in FIGS. 1A and 1B includes a support member (101) wherein the support member has at least one sensor (102) attached to an end of the support member (101), also referred to herein as a "peg". A support member may be formed and then attached to another substrate by fasteners, bonding, ultrasonic welding, and the like. A support member can also be formed as part of another substrate by machining, molding, and the like. A support member material can be made from any material that is compatible with the chemical reactants, other operating environment (such as temperature) and solvents that may be placed in contact with the support member. The material of a support member can be different than the material of the sensor. Any of a variety of organic or inorganic materials or combinations thereof, may be employed for a support member including, for example, metals, plastics, such as polypropylene, polystyrene, polyvinyl chloride, polycarbonate, polysulfone, nylon, teflon, ceramic, silicon, (fused) silica, quartz or glass, and the like. A support member may be solid, semi-rigid, flexible or a combination thereof and be of any shape. The shape of a support member may be, for example, rectangular, diamond, square, circular, oval, any modifications thereof and so forth. Examples of different shaped support members (101) are shown in FIGS. 2A to 2C. A support member (101) can be solid, hollow, or partially hollow and the sensor can be attached at either side. The shape and size of one end of a support member (101) where a sensor is attached can be similar to that of the sensor.

In another preferred embodiment, the pegs (101) are designed and assembled to allow a plurality of sensors to be processed at one time. The dimensions of a peg can depend on the size of the sensor, the number of sensors to be processed at one time and the method and apparatus used for further processing. For example, some process steps may require the sensor to be submerged into a well with liquid. During the immersing process, unwanted bubbles may form. There are several ways to prevent bubbles from appearing or to remove bubbles, for example, degassing of the solution, redesign of the receiving chamber, by using a hydrophobic or hydrophilic coating, and by the design of the wells. Another way is to modify the structure of the peg according to an embodiment of the present invention.

In another aspect of the invention, the support member has sloped side walls to reduce or prevent the formation of bubbles in a liquid sample during contact with the sensor and during the mixing of a liquid sample. There are several ways in which bubbles can be created. For example, bubbles can be created during an insertion of a support member and sensor, sometimes referred to as a sensor peg, and an introduction of a liquid into the well. In some cases, a heat source is employed to provide appropriate hybridization temperature. Heating of the sample may also create bubbles. In one embodiment, the support member is sloped such that the top is narrow and then widens at the bottom where the sensor is attached, see FIG. 1A. This may allow sufficient volume for gas to expand such that the bubbles diffuse at the surface of the liquid.

The methods and apparatus are suitable for various types of sensors, such sensors may include "nucleic acid sensors" such as nucleic acid microarrays. In a preferred embodiment, the sensor can be a microarray such as a cDNA array, a peptide array, a bead array or an in situ synthesized high density oligonucleotide array that may be in situ synthesized. The microarrays can include a substrate. In a preferred embodiment the substrate is flat glass or silica. Surfaces on the solid substrate may be composed of the same material as the substrate or a different material. Thus, the surface may be composed of any of a wide variety of materials, for example, polymers, plastics, resins, polysaccharides, silica or silica-based materials, carbon, metals, inorganic glasses, membranes, or any of the above-listed substrate materials. In one embodiment, the surface will be optically transparent and will have surface SI-OH functionalities, such as those found on silica surfaces. The sensor peg can further include a sensor wherein the sensor is a microarray. In one embodiment of the present invention, a sensor peg (100) is provided wherein the support member (101) has sloped walls as mentioned in the previous section to assist in eliminating bubbles and where the end of the support member may be shaped as a square to fit the sensor which is a microarray (102) as shown in FIG. 1A. In another preferred embodiment of the invention, a microarray peg (100) is provided wherein the support member includes a component which assists in the sealing process during hybridization, for example, an o-ring (103). In one aspect of the present invention, a microarray peg (100) is provided wherein the support member includes a component to assist in the depth at which the sensor is placed into solution, for example a ledge (104) as illustrated in FIG. 1B.

Sensor Plate

Figure 3:
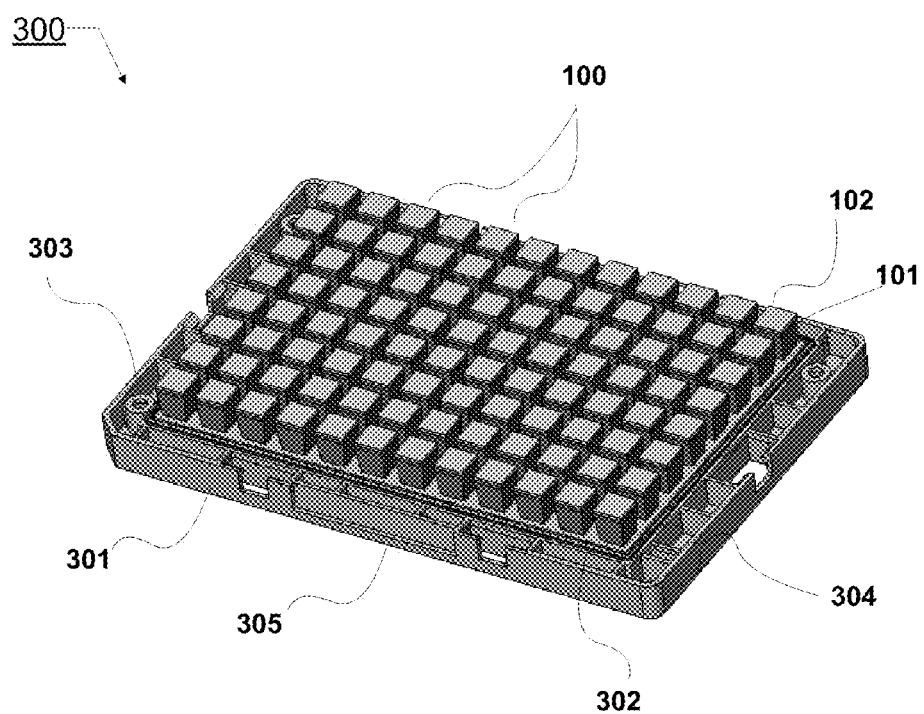
FIG. 3 illustrates an example of a sensor plate with a plurality of sensor pegs.

According to one aspect of the invention, the sensor plate (300) as depicted in FIG. 3, includes a holding device (301) wherein the holding device has a plurality of support members (101) which are pegs (e.g. 12, 24, 36, 96 pegs, etc.), projecting from one side of the holding device (301). In a preferred embodiment, the sensor plate (300) further includes a plurality of sensors (102) that are microarrays attached to the end of the support members (101). In a further embodiment of the invention, the sensor plate includes a sealing surface such as an elastomeric seal (302), alignment hole (303), alignment slot (304) and a clamping feature (305). In another preferred embodiment, the elastomeric seal is a gasket. In another embodiment, the sensors can be placed directly onto the holding device. According to another embodiment, the sensors can be assembled onto a plate by combining sensor strips as discussed in U.S. Patent Application Publication 20060088863, which is incorporated herein by reference in its entirety for all purposes.

The holding device material can be made from any material that is compatible with the chemical reactants and solvents that are placed in the wells. Any of a variety of organic or inorganic materials or combinations thereof, may be employed for the holding device including, for example, metal, plastics, such as polypropylene, polystyrene, polyvinyl chloride, polycarbonate, polysulfone, nylon, Teflon, ceramic, silicon, (fused) silica, quartz or glass, and the like. In a preferred embodiment, the material of the holding device is transparent. The holding device (301) can take on various forms, for example, a rectangular, square, circular, oval, and so forth. The dimensions of the holding device can be sufficient to allow for a desired number of support members and sensors of a predetermined size to be incorporated onto the holding device. The holding device can be formed by machining, molding, mechanical forming, and the like. Preferably, the dimensions of the holding device are about 10 mm to about 400 mm in length, about 10 mm to about 400 mm in width, and about 0.25 mm to about 25 mm in depth.

In circumstance where the reaction requires a high hybridization temperature and cold temperature storage, the holding device can be made of any material which can withstand high temperatures for hybridization and be stored in cold temperatures for storage, for example cyrolite, Hi-Lo acrylic, and polycarbonate, etc.

In one aspect of the present invention, array pegs are attached to the holding device. First, a sensor peg is assembled by bonding a microarray to a support member. A low-fluorescent adhesive at the working emission wavelengths of the hybridized, labeled probe arrays can be used to bond the back surface of the microarray to the top surface of the peg such that the probes on the microarray are not damaged. In one preferred embodiment, the curing process can be performed through the top surface of the microarray, from the side, or a combination thereof to bond the microarray to the support member.

In another preferred embodiment, the holding device material is transparent such that the adhesive connecting the sensor peg to the plate can be light cured from the bottom, through the holding device. In a particularly preferred embodiment, the material of the holding device is a plastic, LEXAN™ HP1 (General Electric), which is a transparent material that can allow the sensor plate to withstand high temperatures for hybridization and cold temperatures for storage.

The design of the holding device of the sensor plate can be such that various sizes of sensors (102) on the support members can be attached. The design of the holding device can also be customized to fit various sizes of sensors. In some embodiments, the holding device can be made of an optically clear/transparent material such that the transparency characteristic can assist in the manufacturing of the sensor plate. The support members can also be made of a dark, light absorbing material to minimize the background fluorescence during scanning The advantage of having the plate transparent is that it facilitates the viewing of a sample being present.

According to one aspect of the present invention, a method is provided for constructing a sensor plate. A plurality of sensors is produced by dicing a substrate. Support members which have a first end and a second end and plates are provided. First, a sensor from the diced substrate is attached to the first end of the support member. Next, the second end of the support member is attached to a plate. These steps are repeated until the desired sensor plate is produced. In a preferred embodiment, the sensors are microarrays and the support members are pegs.

In one embodiment, a method further includes the attaching steps as bonding steps using a curable low fluorescence adhesive. According to another aspect of the invention, the adhesive is cured with a solid state narrow wavelength light source. In a preferred embodiment, the light source is a blue LED. More preferably, the LED's wavelength is from 430 nm to 480 nm and most preferably, the wavelength is approximately 455 nm.

Inspection Tool

Figure 4:
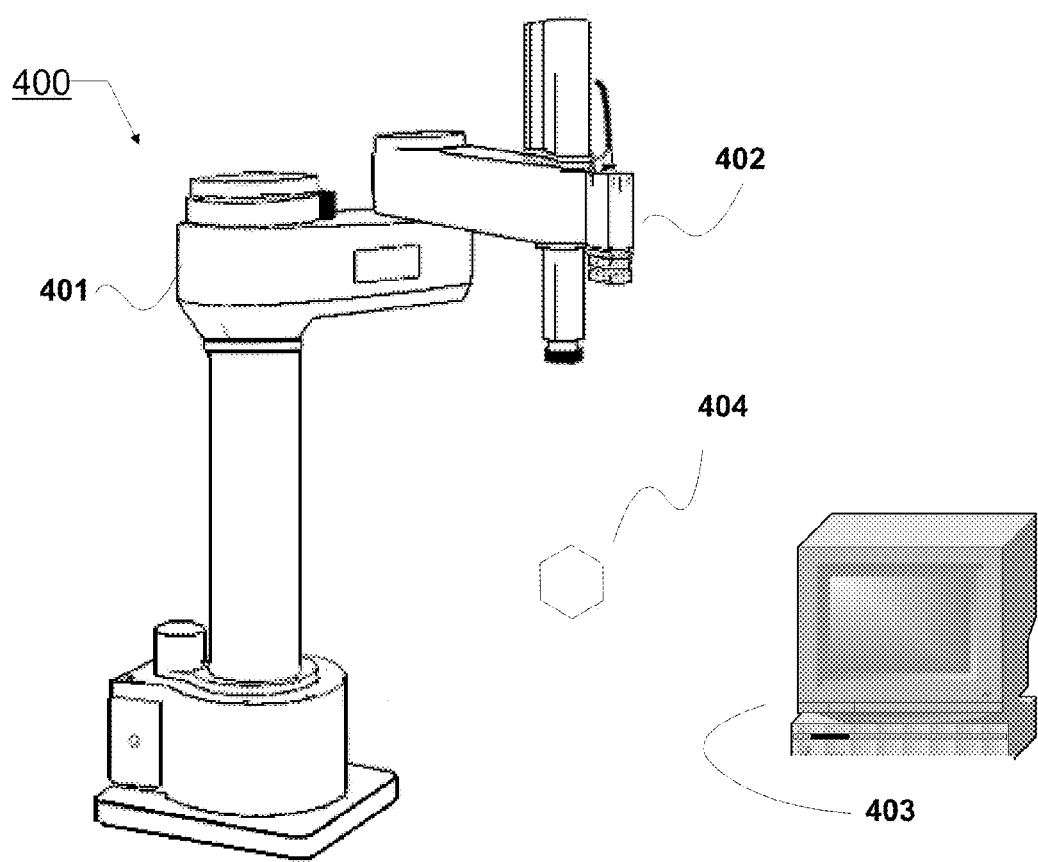
FIG. 4 illustrates an example of an inspection tool.

FIG. 4 illustrates an inspection tool according to an embodiment of the invention. In a preferred embodiment of the present invention, the inspection tool (400) includes a robot (401), a camera (402), and a vision system (403). Vision systems for inspecting components are well known. Examples of manufacturers of vision systems are: Cognex, Matrox, and Omron. The sensor plate assembly process and equipment have been described in U.S. Patent Application Publication 20060082822, which is incorporated herein by reference in its entirety for all purposes. According to a preferred embodiment, the inspection tool or module can be combined with the sensor plate assembly equipment.

Measurements for each component position are made using the inspection tool. In general, the robot (401) moves in the X,Y directions to position the camera above the component (404) to be inspected. An image of the component (404) is taken using the camera (402) and then the measurements are determined using the vision system (403).

The method of the invention is generally capable of carrying out a calibration method to provide an x, y tolerance in the range of 1 to 50 microns according to an embodiment of the invention, preferably in the range of 1 to 30 microns, and most preferably in the range of 3 to 25 microns. In a preferred embodiment, the calibration method uses a calibration plate (500) as depicted in FIG. 5.

Calibration Substrate

Figure 5:
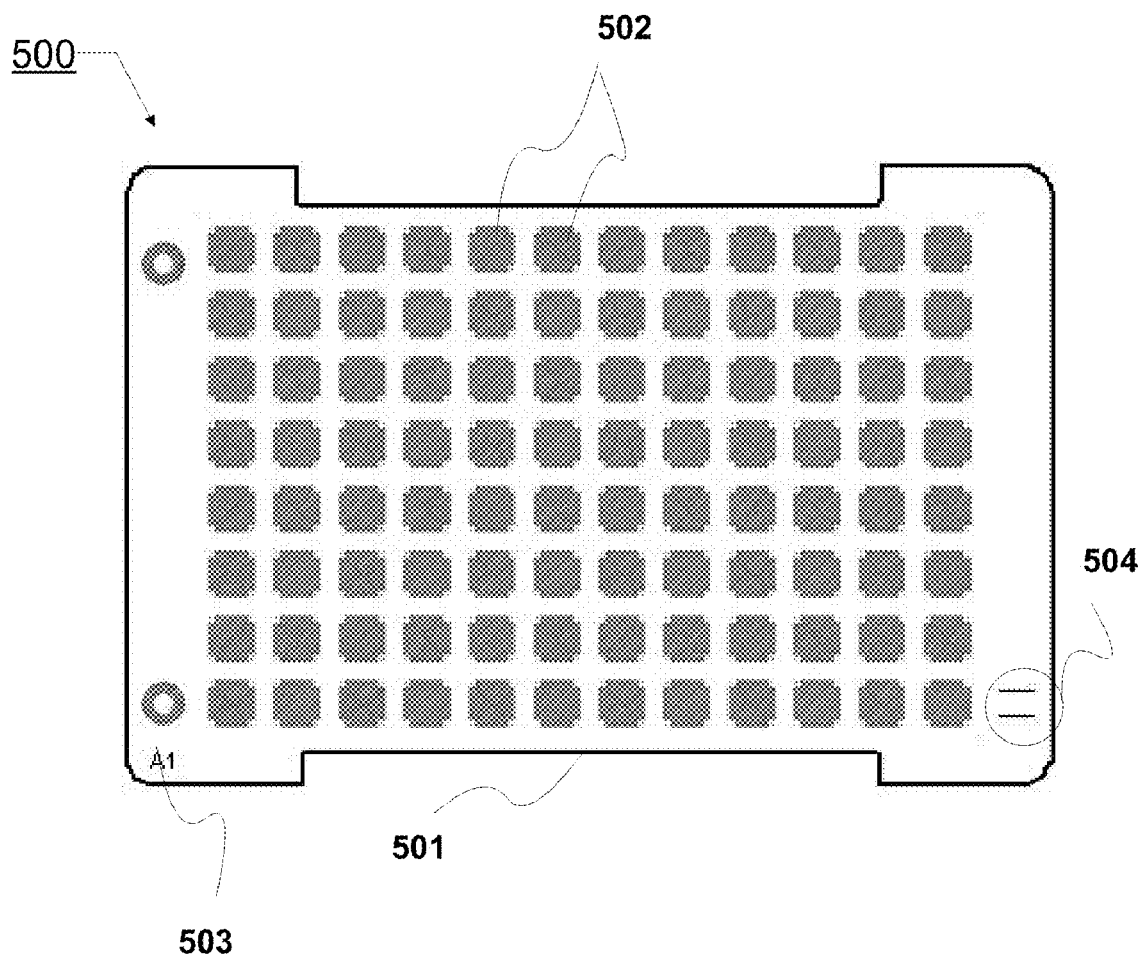
FIG. 5 illustrates an example of a calibration glass plate.

In a preferred embodiment of the invention, the calibration method disclosed herein uses a calibration plate (500) as depicted in FIG. 5. According to one aspect of the invention, the calibration plate (500) includes a plate (501) which includes a plurality of fiducials on one side of the plate. In a preferred embodiment, the plate is made out of glass and the material used to etch the fiducials on the glass plate is chrome. The etched fiducials comprise a plurality of sensor peg locations (502), an alignment hole (503), and an alignment slot (504) according to an embodiment of the present invention. The alignment hole and slot are used to align the substrate onto the vision system with respect to the angle of the substrate being placed into the vision system.

The calibration plate is made according to the theoretical specification of the object to be inspected, for example, the sensor plate. The calibration plate material can be made from any material which can withstand high temperatures, for example silicon, (fused) silica, quartz or glass and the like, according to a preferred embodiment of the present invention. The material of the calibration plate is preferably transparent. Preferably, the dimensions of the calibration plate are about 10 mm to about 400 mm in length, about 10 mm to about 300 mm in width, and about 0.25 mm to about 30 mm in depth. More preferably, the dimensions of the calibration plate are about 50 mm to about 300 mm in length, about 50 mm to about 200 mm in width, and about 5 mm to about 25 mm in depth. Most preferably, the dimensions of the calibration plate are about 130 mm in length, about 90 mm in width and 20 mm in depth.

The sensor peg location fiducials (502) are certified by the vendor be to within 3 microns of their theoretical location according to a preferred embodiment of the present invention. The shape of the fiducials can take on various forms, for example, a rectangle, square, circular, oval, and so forth. According to another embodiment of the present invention, the dimensions of the fiducials are sufficient to allow the center of the configuration to be detected by a vision system. The fiducials can be formed by machining, molding, mechanical forming, and the like.

Calibration Method—Determining Calibration Offset Factors

Figure 6:
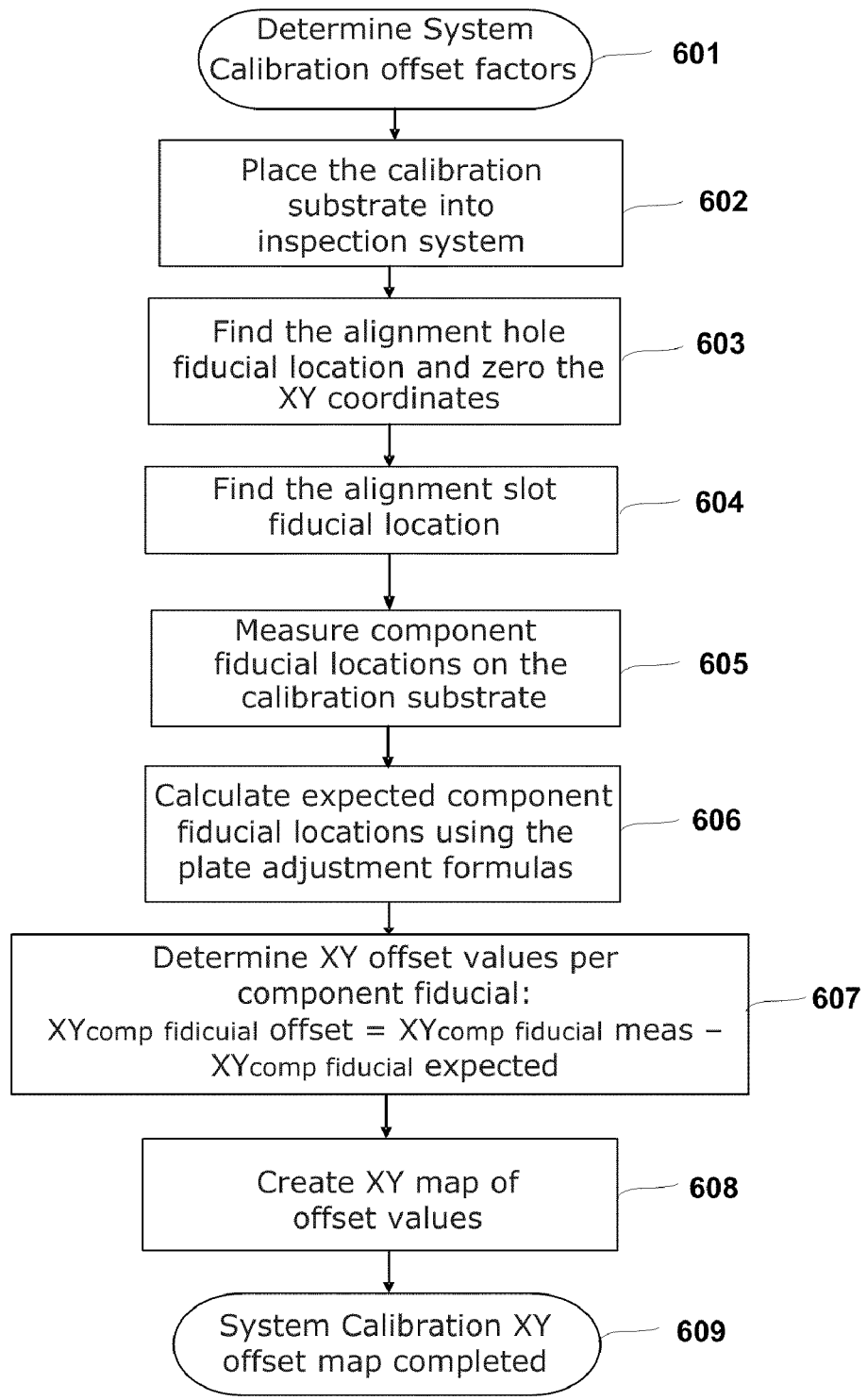
FIG. 6 illustrates an outline of the steps to determine the system calibration offset factors.

The system calibration can be performed by following the steps outlined in FIG. 6 (601 to 609) according to a preferred embodiment of the present invention. After the calibration substrate is placed into the inspection system (602), the robot arm moves the camera over the component to be inspected. The alignment hole fiducial (503) is located and the XY coordinates zeroed (603). The coordinate system of the calibration substrate is specific to the orientation of each substrate. Therefore, the alignment slot fiducial (504) is located (604) and then all the component fiducial locations (502) are measured. Each of the component fiducial locations (502) on the calibration plate (500) are measured using the vision system to obtain the measured X,Y values (605), for example, by taking an image of each component fiducial and locating the XY center of each component fiducial. The expected X,Y values for each component fiducial are calculated using the plate adjustment formulas (606) indicated below:

First, the calibration (Cal) plate angles, the theoretical and experimental angles of each component (Comp) fiducial are calculated using the following formulas:

Cal Substrate Angle_Meas=asin($Y_{Slot\_Meas}/X_{Slot\_Theo}$)

Comp Fiducial Angle_Theor=atan($Y_{Comp\ Fiducial\_Theor}/X_{Comp\ Fiducail\ Theor}$)

Comp Fiducial Angle_Exp=Comp Fiducial Angle_Theor−Cal Substrate Angle_Meas

The theoretical values are based on the specifications of the object being inspected, for example, a sensor array plate. Each of the expected component fiducial locations, adjusted to the plate angle is calculated by using the formulas listed below:

Comp Fiducial Length=sqrt($X^2_{Comp\ Fiducial\_Theor}$+$Y^2_{Comp\ Fiducial\_Theo}$)

$X_{Comp\ Fiducial\ Expected}$=Comp Fiducial Length*cos(Comp Fiducial Angle_Exp)

$Y_{Comp\ Fiducial\ Expected}$=Comp Fiducial Length*sin(Comp Fiducial Angle_Exp)

The XY offset for each component fiducial location on the Calibration substrate can be calculated by using the following formula (607):

$XY_{Comp\ Fiducial\ Offset}=XY_{Comp\ Fiducial\ Measured}-XY_{Comp\ Fiducial\ Expected}$ After the XY offset values for each component fiducial location are determined, the values are incorporated into an XY offset map (608) to be used to determine the actual XY offsets of each component locations relative to their theoretical locations according to an embodiment of the present invention.

Method of Determining "Actual XY Offset Values" for Each Component Location

Figure 7:
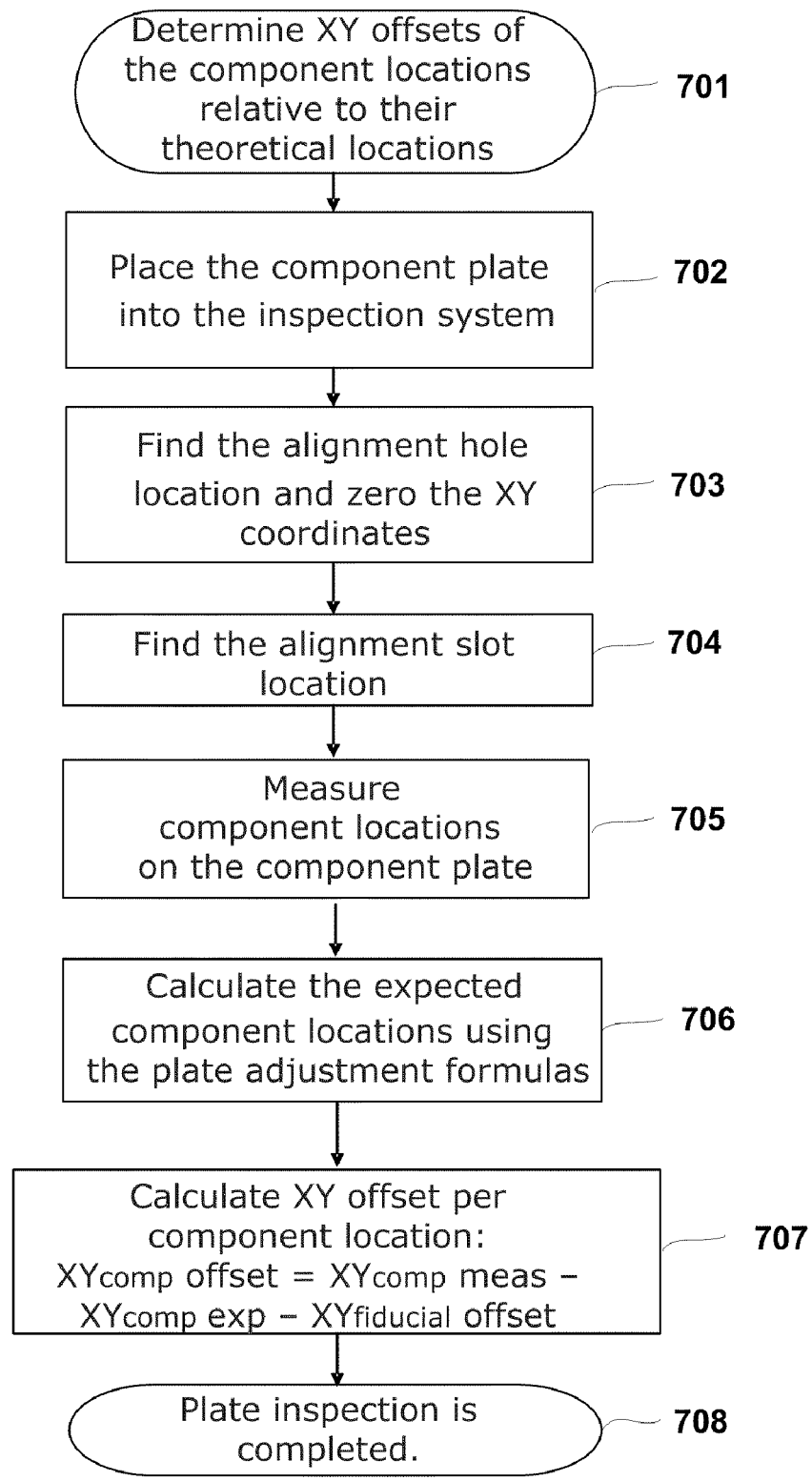
FIG. 7 illustrates an outline of the steps to determine the actual XY offsets of the component locations relative to their theoretical locations by taking the XY calibration offset values into account.

FIG. 7 illustrates an outline showing the steps (701 to 708) to obtain the actual XY offset values of the component locations relative to their theoretical locations according to an embodiment of the present invention. The component plate is placed into the inspection system (702). The plate is aligned by locating the alignment hole and zeroing the XY coordinates with respect to the alignment hole. Once the alignment slot is located (704), each of the component locations on the plate is measured using the vision system (705). The robot arm moves the camera over the component to be inspected. An image of the component is taken and the XY location of the center of the component is measured. The expected X,Y values for each component are calculated using the plate adjustment formulas (706) indicated below:

First, the component (Comp) plate angle, the theoretical and the experimental angles of each component (Comp #) are calculated using the following formulas:

Comp Plate Angle_Meas(A)=asin($Y_{Slot\_Meas}$(811)/$X_{Slot\_Theor}$(812))

Comp Angle_Theor(B)=atan($Y_{Comp\_}$Theor(813)/$X_{comp\_Theor}$(814))

Comp Angle_Exp(C)=Comp Angle_Theor(B)−Comp Plate Angle_Meas(A)

The theoretical values are based on the specifications of the object being inspected, for example, the component plate. Each of the expected component locations adjusted to the Plate angle are calculated by using the formulas listed below:

Comp Length(D)=sqrt($X^2_{Comp\_Theor}$(813)+$Y^2_{Comp\_Theor}$(814))

$X_{Comp\ Expected}$(E)=Comp Length(D)*cos(Comp Angle_Exp(C))

$Y_{Comp\ Expected}$(F)=Comp Length(D)*sin(Comp Angle_Exp(C))

Figure 8:
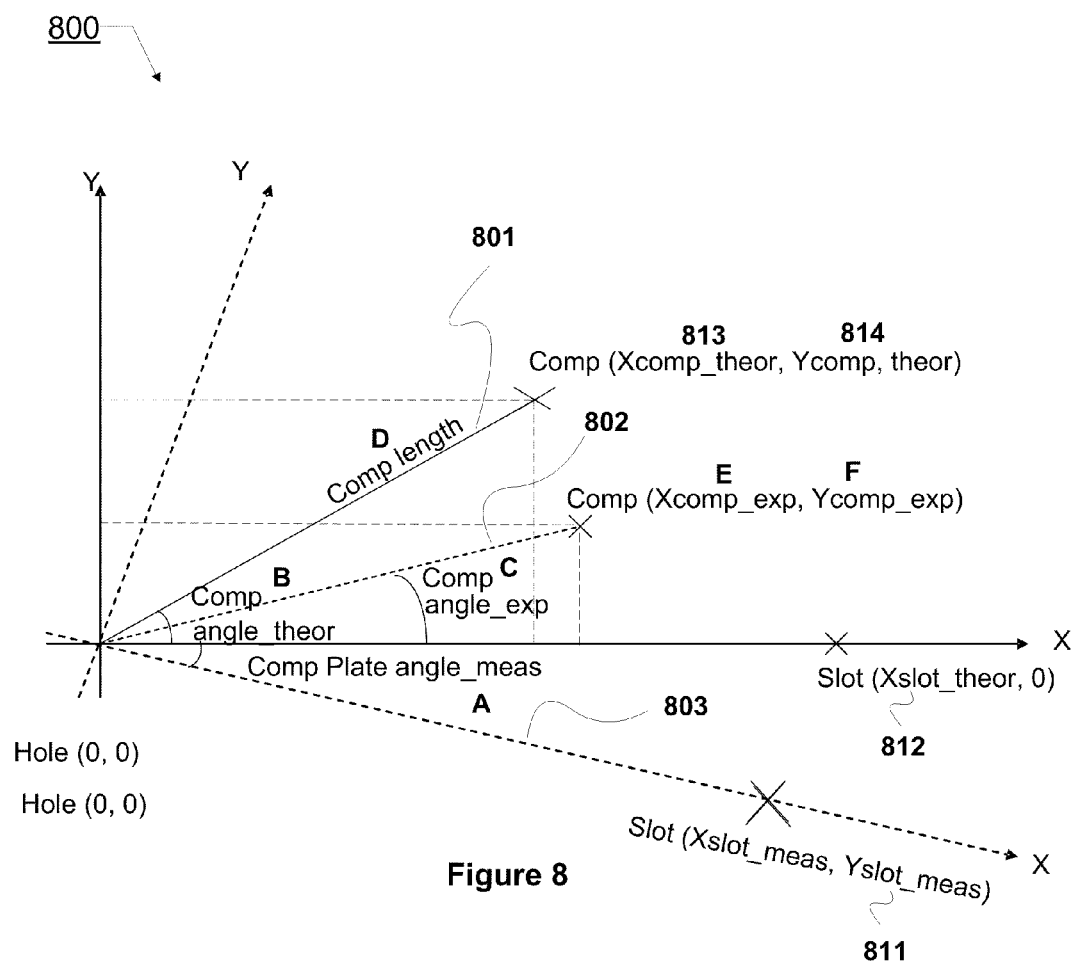
FIG. 8 illustrates the values generated from the plate coordinate system adjustment formula in an XY coordinate system.

The results are displayed in a XY coordinate system as shown in FIG. 8, which provides examples of theoretical, measured and expected values generated from the plate coordinate system adjustment formula in an according to an embodiment of the present invention. The solid line (801) represents the theoretical values. Typically, the theoretical values correspond to the specifications of the part being inspected. The dashed lines (802 and 803) represent the measured and expected object locations.

The actual XY offset values of each of the components on the component plate are calculated (707) by using the following formula:

$XY_{Comp}$Offset=$XY_{Comp\ Measured}-XY_{Comp\ Expected}-XY_{Comp\ Fiducial\ Offset}$ Acceptance criteria for XYoffset values can be created to determine whether or not a component passes inspection.

According to an embodiment of the present invention, a method for calibrating an inspection tool that inspects a plurality of components on a substrate is provided. The calibration methods includes the steps of (1) supporting a calibration substrate comprising a plurality of component fiducials, wherein each component fiducial indicates a theoretical location of each component that is to be inspected, (2) moving a camera over a first component fiducial, by moving the camera in X,Y directions, (3) imaging the first component fiducial on the calibration substrate, (4) measuring an X and a Y position for the first component fiducial on the calibration substrate, (5) calculating a pair of offset values for the X, Y position of the first component fiducial by utilizing the measured X,Y position of the first component fiducial. Steps 1-5 are repeated on each of the component fiducials until the pairs of offset values for all the component fiducials are calculated. The pairs of calibration offset values are placed in an XY map. Calibrated XY offset values for each component in the XY map are used during the inspection of a plurality of components on the substrate according to another embodiment of the present invention. In a preferred embodiment the calibration substrate is made of glass and the fiducials are etched onto the glass substrate. According to another preferred embodiment of the present invention, the plurality of component fiducials on the calibration substrate is within 3 microns of their theoretical location. In one embodiment of the present invention, the component substrate to be inspected is a sensor plate where the components are array pegs and the sensors are biological microarrays.

According to another embodiment of the invention, a method to determine actual XY locations of components is provided. In a preferred embodiment, a method of determining actual XY locations of array pegs on an HTA plate is provided. The component plate is placed into the inspection system, where the vision system locates the alignment features, for example, a hole, slot, etc. The coordinates are zeroed. The location of each component is measured. The expected component locations are calculated using the plate adjustment formulas. The XY actual offset value of each component is calculated by subtracting the XY expected value and the XY calibration offset value from the XY measured value for each component.

According to another embodiment, a system for calibrating an inspection tool that inspects a plurality of components on a substrate is provided. The system includes a table for supporting a calibration substrate comprising a plurality of component fiducials, wherein each component fiducial indicates a theoretical location of each component that is to be inspected. A camera is used to view the plurality of component fiducials. A robot moves the camera in an X,Y directions such that the camera is over looking each component fiducial for inspection. A vision system is used to image each component fiducial on the calibration substrate. A measuring device is used to measure an X, Y position for each component fiducial on the calibration substrate. A processor is used to calculate a calibration offset location for the X, Y position of each component fiducial. A computer is used to place the calibration offset values in an XY map which is used as a source for calibrated XY offset values per each component fiducial for inspecting the plurality of components on the substrate. In a preferred embodiment the calibration substrate is made of glass and the fiducials are etched onto the glass substrate. According to another preferred embodiment of the present invention, the plurality of component fiducials on the calibration substrate is within 3 microns of their theoretical location. In one embodiment of the present invention, the component substrate to be inspected is an sensor plate where the components are array pegs and the sensors are biological microarrays.

In a preferred embodiment, the locations of array pegs on an HTA plate are inspected by determining the actual offset of the locations of the array pegs relative to their theoretical locations. A calibration substrate is fabricated based on the product specification of the peg plate. The inspection system is calibrated with the calibration substrate before measuring the array pegs on the peg plate. The calibration substrate is placed into the inspection system and the component fiducials are measured. The expected XY locations of the component fiducials (XYs—component fiducial expected) are calculated using the plate adjustment formula described above. The calibration offset values are determined by subtracting the expected XY locations of the fiducials on the calibration substrate from the measured locations. The calibration substrate is then removed and replaced with an HTA plate to be inspected. The location of the array pegs are measured and the expected XY locations of the array pegs (XYs—array pegs expected) are calculated using the plate adjustment formula described above. The actual offset values of the locations of the array pegs relative to their theoretical locations are determined by subtracting the expected XY locations of the array pegs on the HTA plate and the calibration offset values from the measured locations of the array pegs on the HTA plate.

In another aspect of the invention, an apparatus for calibrating an inspection tool that inspects a plurality of components on a substrate is provided. The following components are included in this apparatus: (a) A first component for receiving a calibration substrate comprising a plurality of component fiducials, one fiducial per component, wherein each fiducial indicates a theoretical location of each component that is to be inspected, (b) a second component for moving a camera in an X direction and Y direction over a first component fiducial, (c) a third component for moving a camera in an X direction and a Y direction over the first component fiducial, (d) a fourth component for imaging the first component fiducial on the calibration substrate, (e) a fifth component for measuring an X direction and a Y direction over the first component fiducial, (f) a sixth component for calculating a pair of XY offset value for the X,Y position of the first component fiducial by utilizing the measured X,Y positions of the first component fiudical, (7) a seventh component for repeating the moving, imaging, measuring and calculating steps on each of the component fiducials until the pairs of the XY calibration offset values for the component fiducials are calculated, and (8) an eighth component for placing the pairs of XY calibration offset values in an XY map; and using the XY map as a source of calibrated XY offset values for each component when inspecting the plurality of components on the substrate.

EXAMPLES

Example 1

Creating a System Calibration XY Offset Map

A system calibration XY offset map was created for inspecting arrays (102) on an array plate (300) as illustrated in FIG. 3 by following the steps outlined in FIG. 6 according to an embodiment of the present invention. According to a preferred embodiment, Affymetrix GENECHIP® probe arrays on a GENECHIP® HT Array (HTA) Plate were inspected. A calibration substrate was made using the theoretical specification of the array plate to be inspected. The calibration substrate was made out of glass and included etched chromed fiducials as illustrated in FIG. 5. The etched fiducials comprised of an alignment hole (503), an alignment slot (504) and 96 array peg fiducials (502) that corresponded to the 96 array pegs on the HTA plate to be inspected. The calibration substrate was placed into the inspection system (602). Once the alignment hole fiducial was located, the XY coordinates of motion was zeroed (603) and the alignment slot fiducial was located (604). Each of the 96 array peg fiducial locations on the calibration substrate was measured using a vision system (605). The expected array peg fiducial locations were then calculated using the plate adjustment formulas (606). The XY calibration offset values for each array peg were determined (607) and placed into an XY map (608) to complete the system calibration XY offset map.

Example 2

Using the Calibration Method to Inspect Array Pegs on a Plate

GENECHIP® probe arrays on a GENECHIP® HT Array (HTA) Plate were inspected using the calibration method as outlined FIG. 7 according to an embodiment of the present invention. The actual XY offset of the array pegs relative to their theoretical were determined (701) by utilizing the calibration substrate described in example 1 above. The array plate was placed in the inspection system (702). Once the alignment hole was located, the XY coordinates of motion was zeroed (703) and the alignment slot was located (704). Each of the 96 array peg locations on the array plate were measured using the vision system (705). The expected array peg locations were then calculated using the plate adjustment formulas (706). The actual XY offset for each array peg were determined (707) by subtracting the expected and calibration offset XY values from the measured XY values of each array peg on the array plate.

IV. Conclusion

It is to be understood that the above description is intended to be illustrative and not restrictive. Many variations of the invention will be apparent to those of skill in the art upon reviewing the above description and figures. All cited references, including patent and non-patent literature, are incorporated by reference herein in their entireties for all purposes.

What is claimed is:

1. A method for generating calibration data for an inspection apparatus, the method comprising:
   providing a calibration substrate, wherein the calibration substrate comprises a plurality of component fiducials;
   (a) moving a camera over a first component fiducial;
   (b) imaging, with a vision system, the first component fiducial, wherein the vision system includes the camera;
   (c) measuring, with the vision system, an X position and a Y position for the first component fiducial;
   (d) calculating, with a computer, an X calibration offset value and a Y calibration offset value of the first component fiducial, wherein the X calibration offset value is based upon the X position, and wherein the Y calibration offset value is based upon the Y position;
   repeating steps (a)-(d) for each of the component fiducials to generate pairs of XY calibration offset values for the plurality of component fiducials; and
   placing, with the computer, the pairs of XY calibration offset values in an XY map.

2. A system for generating calibration data for an inspection apparatus, the system comprising:
   a calibration substrate, wherein the calibration substrate comprises a plurality of component fiducials;
   a vision system configured to view the plurality component fiducials, wherein the vision system comprises a camera, and wherein the vision system is configured to image the plurality of component fiducials and measure an X position and a Y position for each component fiducial;
   a robot configured to move the camera over each component fiducial; and
   a computer, wherein the computer is configured to calculate an X calibration offset value and a Y calibration offset value of each component fiducial, wherein the X calibration offset value is based upon the X position, and wherein the Y calibration offset value is based upon the Y position, and wherein the computer is additionally configured to place the X calibration offset values and the Y calibration offset values in an XY map.

3. The method of claim 1, wherein the calibration substrate comprises one or more alignment features, and wherein the one or more alignment features are used by the vision system in measuring the X position and Y position of the first component fiducial.

4. The method of claim 3, wherein the one or more alignment features are used by the vision system as a reference point for the X position and the Y position of the first component fiducial.

5. The method of claim 3, wherein the one or more alignment features are used in calculating one or more alignment feature angles for comparison with one or more fiducial component angles calculated based upon the first component fiducial, and wherein the comparison is used by the computer within calculations of the X calibration offset value and the Y calibration offset value.

6. The method of claim 3, wherein the one or more alignment features include a first alignment feature and a second alignment feature, wherein the first alignment feature is used by the vision system as a reference point for the X position and the Y position of the first component fiducial, wherein the first and second alignment features are used by the vision system and the computer in measuring and calculating an experimental component fiducial angle, and wherein the experimental component fiducial angle is used by the computer within calculations of the X calibration offset value and the Y calibration offset value.

7. The method of claim 1, wherein the X calibration offset value is additionally based upon an expected X position, and wherein the Y calibration offset value is additionally based upon an expected Y position.

8. The method of claim 6, wherein the expected X and Y positions are based upon theoretical values, and wherein the theoretical values are retrieved by the computer based upon the calibration substrate.

9. The method of claim 6, wherein measuring and calculating the experimental component fiducial angle comprises:
   measuring and calculating a calibration substrate angle based upon the first and second alignment features; and
   calculating the experimental component fiducial angle based upon a difference between a theoretical component fiducial angle and the calibration substrate angle, wherein the theoretical component fiducial angle is based upon an expected X position and an expected Y position.

10. The method of claim 9, wherein the X calibration offset value is based upon the X position, the expected X position and the experimental component fiducial angle, and wherein the Y calibration offset value is based upon the Y position, the expected Y position and the experimental component fiducial angle.

11. The system of claim 2, wherein the calibration substrate comprises one or more alignment features, and wherein the vision system and computer are additionally configured to image and measure the X position and the Y position of the first component fiducial based upon the one or more alignment features.

12. The system of claim 11, wherein the vision system is configured to utilize the one or more alignment features as a reference point for the X position and the Y position of the first component fiducial.

13. The system of claim 11, wherein the computer is additionally configured to calculate and compare one or more alignment feature angles based upon the one or more alignment features and one or more component fiducial angles based upon the first component fiducial, and wherein the comparison is used by the computer within the calculations of the X calibration offset value and the Y calibration offset value.

14. The system of claim 11, wherein the one or more alignment features include a first alignment feature and a second alignment feature, wherein the vision system is configured to use the first alignment feature as a reference point for the X position and the Y position, wherein the vision system and computer are additionally configured to use the first and second alignment features in calculating an experimental component fiducial angle, and wherein the computer is additionally configured to use the experimental component fiducial angle within calculations of the X calibration offset value and Y calibration offset value.

15. The system of claim 2, wherein the computer is additionally configured to calculate the X calibration offset value based upon an expected X position and the Y calibration offset value based upon an expected Y position.

16. The system of claim 15, wherein the expected X and Y positions are based upon theoretical values, and wherein the computer is additionally configured to retrieve the theoretical values based upon the calibration substrate.

17. The system of claim 14, wherein the vision system and the computer are additionally configured to measure and calculate a calibration substrate angle based upon the first and second alignment features, and wherein the computer is additionally configured to calculate the experimental component fiducial angle based upon a difference between a theoretical component fiducial angle and the calibration substrate angle, wherein the theoretical component fiducial angle is based upon an expected X position and an expected Y position.

18. The system of claim 17, wherein the computer is additionally configured to calculate the X calibration offset value based upon the X position, the expected X position and the experimental component fiducial angle, and wherein the computer is additionally configured to calculate the Y calibration offset value based upon the Y position, the expected Y position and the experimental component fiducial angle.

* * * * *